US011612771B2

United States Patent
Singer

(10) Patent No.: US 11,612,771 B2
(45) Date of Patent: Mar. 28, 2023

(54) HEAD ENCAPSULATION UNIT

(71) Applicant: Nicholas J. Singer, Irvine, CA (US)

(72) Inventor: Nicholas J. Singer, Irvine, CA (US)

(*) Notice: Subject to any disclaimer, the term of this patent is extended or adjusted under 35 U.S.C. 154(b) by 0 days.

(21) Appl. No.: 16/874,492

(22) Filed: May 14, 2020

(65) Prior Publication Data

US 2021/0331002 A1 Oct. 28, 2021

Related U.S. Application Data

(63) Continuation of application No. 16/855,309, filed on Apr. 22, 2020.

(51) Int. Cl.
*A62B 18/04* (2006.01)
*A61M 16/10* (2006.01)

(52) U.S. Cl.
CPC ......... *A62B 18/04* (2013.01); *A61M 16/1055* (2013.01); *A61M 2205/7509* (2013.01)

(58) Field of Classification Search
CPC ... A62B 18/00; A62B 18/02; A62B 18/04–06; A62B 23/00; A62B 23/02; A62B 17/00; A62B 17/006; A62B 17/04; A61M 16/105; A61M 2205/75–7518; A61M 16/10; A61M 16/1055–107; A41D 13/11; A41D 13/1107; A41D 13/1153–1192; A42B 1/002; A42B 1/046; A42B 1/20; A42B 1/201
See application file for complete search history.

(56) References Cited

U.S. PATENT DOCUMENTS

| | | | | |
|---|---|---|---|---|
| 1,004,507 A | * | 9/1911 | Walz | A42B 1/046 2/4 |
| 1,939,188 A | * | 12/1933 | Schleich | A62B 18/04 128/201.23 |
| 2,181,159 A | * | 11/1939 | Temple | B63C 9/093 441/103 |
| 2,296,338 A | * | 9/1942 | Dakin | A62B 18/04 128/201.15 |
| 3,958,275 A | * | 5/1976 | Morgan | B63C 11/06 128/201.27 |
| 5,016,625 A | * | 5/1991 | Hsu | A62B 17/04 128/206.16 |
| H1316 H | * | 6/1994 | McGuinness | 128/201.15 |
| 5,864,887 A | * | 2/1999 | Kozawa | A45D 8/40 2/202 |

(Continued)

*Primary Examiner* — Michelle J Lee
(74) *Attorney, Agent, or Firm* — KOS IP Law LLP

(57) ABSTRACT

A head encapsulation unit is disclosed which filters virus contaminated air. The head encapsulation unit does not require a fitting process since the primary interface between the head encapsulation unit and the user is the user's neck. The head encapsulation unit has an expandable seal that a user can insert his or her head. The seal is then wrapped around and places light pressure against the person's neck so that virus contaminated air that does not enter the inner volume of the head encapsulation unit and infect the user. A cap at the upper portion of the unit and the seal aligns the head encapsulation unit on the user's head. This head encapsulation unit allows for both medical personnel and infected individuals to better and more easily communicate than mouth covered filters, goggles and face shield while offering substantially more mitigation from spreading an infection or being infected.

14 Claims, 9 Drawing Sheets

(56) References Cited

U.S. PATENT DOCUMENTS

| | | | | |
|---|---|---|---|---|
| 6,134,716 A | * | 10/2000 | Richardson | A41D 13/1153 2/202 |
| 2021/0298385 A1 | * | 9/2021 | Hays | A62B 23/025 |
| 2021/0331001 A1 | * | 10/2021 | Singer | A62B 18/04 |

* cited by examiner

HEAD ENCAPSULATION UNIT

CROSS-REFERENCE TO RELATED APPLICATIONS

This application is a continuation of U.S. patent application Ser. No. 16/855,309, filed on Apr. 22, 2020, the entire contents of which is expressly incorporated herein by reference.

STATEMENT RE: FEDERALLY SPONSORED RESEARCH/DEVELOPMENT

Not Applicable.

BACKGROUND

The various aspects described herein relate to a head encapsulation unit for protecting a user from spreading or breathing in harmful viruses. The head encapsulation unit can be easily put on and sealed without any extensive training in the event of an emergency or pandemic.

Many devices exist in the marketplace that filter contaminated air so that the user does not inhale harmful viruses and bacteria that may be in the air. However, these devices suffer from certain deficiencies so that they still leave the user vulnerable to infection from the harmful virus. For example, these prior art devices may not form a sufficient seal with the person skin because of facial hair. The harmful virus may bypass the filtering mechanism of the device and be inhaled by the user through an air pathway formed at the interface between the device and the person's skin. Sometimes, a seal is broken between the device the person's skin when the user talks, smiles, coughs or sneezes. These facial movements break the seal and allow unfiltered air which may be contaminated to bypass the filtering mechanism of the prior art device. Moreover, these prior art devices leave the eyes and ears exposed to harmful viruses and bacteria (i.e., microorganisms). These and other prior art devices suffer from these and other deficiencies.

Accordingly, there is a need in the art for an improved device that a user can wear for filtering viruses and from the user spreading harmful viruses.

BRIEF SUMMARY

The various aspects of the head encapsulation unit discussed herein relate to a device that can be worn over a person's head. The head encapsulation unit may be positioned on the user's head by way of a cap and a seal. The cap is disposed inside the head encapsulation unit and fits on top of the person's head. The seal is at a bottom portion of the head encapsulation unit and sealingly engages the person's neck. The cap and the seal positions the rest of the parts of the head encapsulation unit to the user's head and face. The head encapsulation unit has a body (i.e., housing, frame and front transparent layer) with cutouts. A filtering mechanism is mounted to the cutouts. The filtering mechanism allows the person to breathe filtered air since the filtering mechanism traps harmful contaminants such as viruses. The seal is easy to wrap around the user's neck and does not require extensive training and fitting to ensure that contaminated air is not transferred into the head encapsulation unit via the interface between the seal and the user's neck. Moreover, the frontal area of the head encapsulation unit may be transparent to allow the user to speak freely without fear of contaminated air seeping into the mask when the user speaks, makes a facial expression or through faulty fitting of the device to a user's anatomical features. The head encapsulation unit also when worn by an infected person would traps viruses in the head encapsulation unit so that the infected person is not spreading harmful viruses when the contagious.

More particularly, a head encapsulation unit for mitigating contact of an airborne virus from contacting mucous membranes of the eyes, nose and mouth is disclosed. The head encapsulation unit may comprise a body, a filter, and a seal.

The body may define an interior volume. The body may include a bottom portion, a transparent front panel having a first cutout, and a top portion.

The filter may be removably attachable to the first cutout.

The seal may be attached to the bottom portion of the body. The seal may include a strap, a base, and a cushion.

The strap may be removably attachable to the base. A through hole in the bottom portion of the body may be sufficiently large so that a person's head may be inserted through the through hole of the bottom portion so that the person can wear the head encapsulation unit. The cushion may provide a seal against a user's neck when the strap is pulled and attached to the base.

The body discussed herein may include a housing and a transparent layer. The body may be fabricated from a resilient and flexible material. The body may be resiliently biased to the expanded position and collapsible to a collapsed position.

The head encapsulation unit may further comprise a strap for holding the housing in the collapsed position for the purposes of storage and transportation. A first end of the strap may be attached to a first side of a frame of the body. A second end of the strap may be removably attached to a second side of the frame of the body.

The bottom portion of the body may be stretchable. In particular, the bottom portion of the body may be stretched out sufficient to allow the user to insert his or head into the inner volume of the body. The cushion of the seal may be fabricated from silicone, vinyl, neoprene or a closed cell foam. When the seal is closed (i.e., strap is tensions and attached to the base), then the cushion forms a seal to mitigate contaminated air from entering the inner volume of the body and the user from spreading viruses when contagious.

The housing may be resiliently biased to the expanded position. In this regard, the housing may be fabricated from a material which is resiliently biased to the expanded position. Alternatively or additionally, the housing may be formed with wire rods that are resiliently biased to form the housing in the expanded position. The wire rods can be bent so that the housing is collapsible to the collapsed position.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
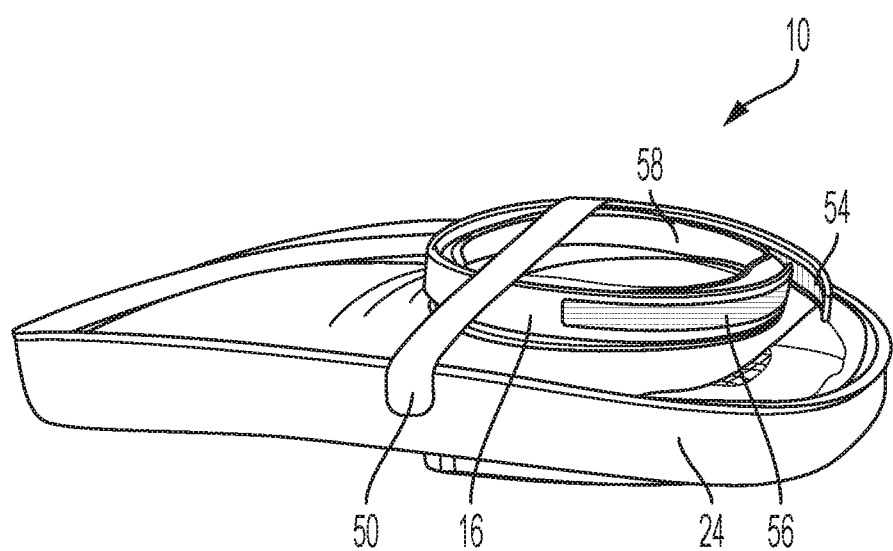
FIG. 1 is a perspective view of a collapsed head encapsulation unit.

Referring now to the drawings, a head encapsulation unit 10 (FIG. 7) which can be worn on a person's head 12 is shown. The head encapsulation unit 10 may be positioned on the user's head 12 by way of a cap 14 and a removably attachable seal 16 that goes around the user's neck 18. The cap 14 and the seal 16 aligns the head encapsulation unit to the user's head. The head encapsulation unit 10 is also generally rigid when it is in the expanded position (FIG. 7) so that air can flow through filters 20, 22. The housing does not flex in and out as a user breathes in and out. Moreover, a front area and sides of the unit may be transparent so that the user can view his or her surroundings when wearing the head encapsulation unit. Because the head encapsulation unit covers the entire person's head, microorganisms, viruses, dust and other micro particulates do not enter the person's cavities (e.g., mouth, nasal, eyes, ear cavities). Rather, the user's entire head is protected from environmental organic and nonorganic materials. The filters 20, 22 may be selected to match the level of protected needed by the user. Moreover, when the user is infected with a harmful virus and contagious, the unit prevents the user from spreading the harmful virus.

Figure 7:
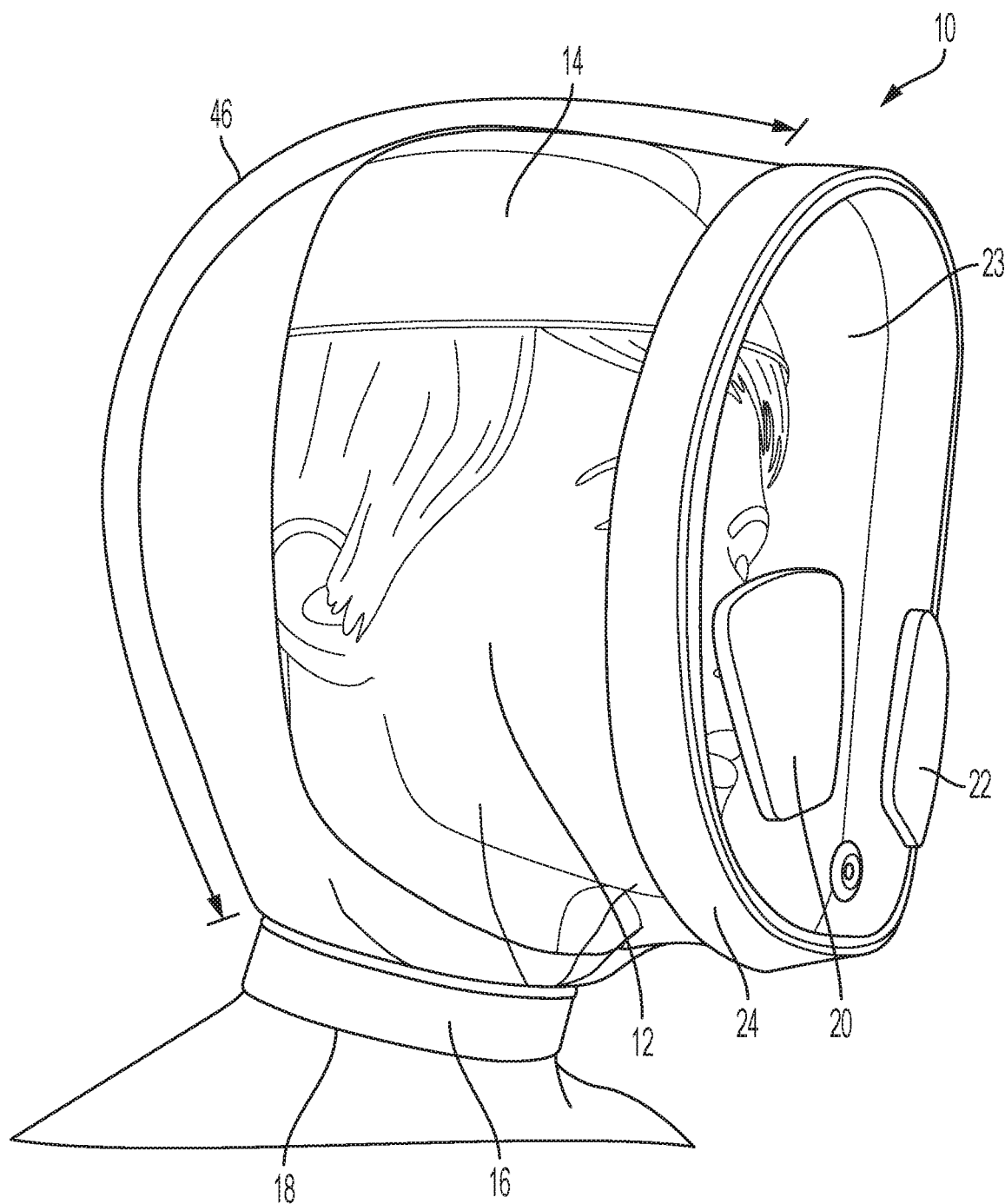
FIG. 7 is a perspective view of the head encapsulation unit being worn by a user.
Figure 8:
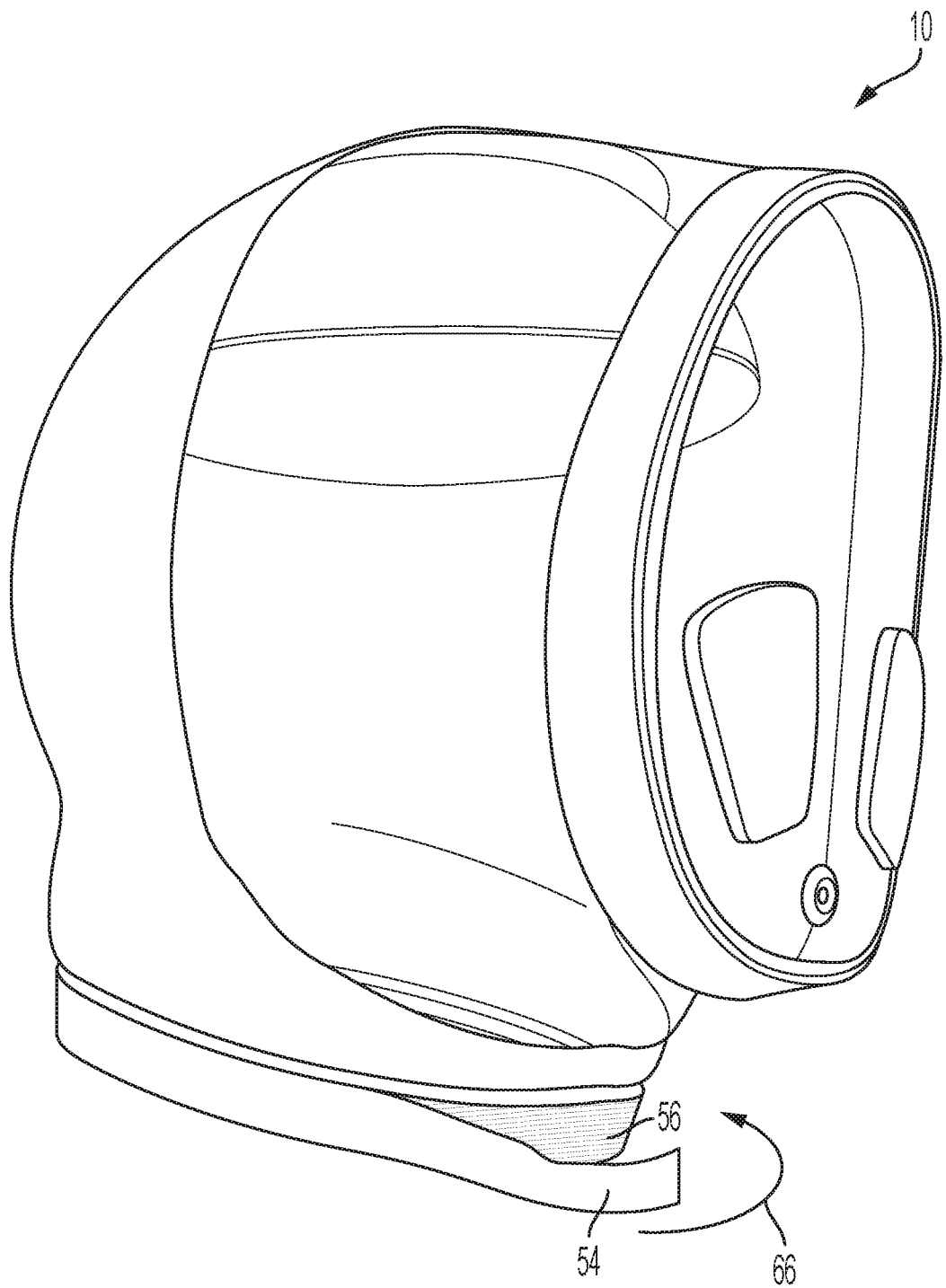
FIG. 8 illustrates a strap removably attachable to a base for securing the seal against a user's neck.

Referring now to FIG. 1, the head encapsulation unit 10 may be provided in a collapsed position. Moreover, the head encapsulation unit 10 may be traversed to the expanded position (FIG. 7). Moreover, the head encapsulation unit 10 may have a rigid frame 24 (FIG. 7). This rigid frame 24 may have a generally oval configuration with a height 26 (FIG. 3) between 8.3 inches and 14 inches but is preferably about 10.5 inches. The rigid frame 24 may also have a width 28 between 5.5 inches and 8 inches and is preferably about 7 inches. The frame 24 may be fabricated from a lightweight material including but not limited to plastic, polymer, composite, and other materials known in the art. Preferably, the rigid frame 24 has a porosity which is lower than the porosity of the filters 20, 22 and is preferably nonporous. The rigid frame 24 may hold its shape regardless of whether is traversed to the expanded or collapsed positions. The front of the rigid frame 24 may have a transparent layer 23. The transparent layer 23 may be fabricated from a nonporous material such as polyethylene, vinyl or plastic. The outer periphery 30 of the transparent layer 23 may be hermetically sealed to the inner periphery 32 of the rigid frame so that micro particulates do not pass from the environment to the interior volume of the head encapsulation unit 10 when worn.

The transparent layer 23 may also have two (2) cutouts 34, 36. These cutouts may receive mounting brackets 38, 40. These mounting brackets 38, 40 are also sealed to the inner periphery of the cutouts 34, 36 so that microorganisms (viruses and bacteria) and microparticulate do not pass from the environment into the interior volume of the head encapsulation unit 10. The filters 20, 22 may be removably mountable to the mounting brackets 38, 40. To aid in the removeable attachment of the filters 20, 22 to the mounting brackets 38, 40, mounting covers 42, 44 may cover the filters 20, 22 and be removably attachable to the mounting brackets 38, 40 via detents.

The filters 20, 22 which are mounted to the mounting brackets 38, 40 may be selected based on the particular use of the head encapsulation unit 10. For example, the filters 20, 22 mounted to the mountain brackets 38, 40 may be an N95 or an N99 filter. These filters are only exemplary and other filters having different ratings for differing sizes and concentration of micro particles may be utilized and mounted to the mountain brackets 38, 40.

Figure 5:
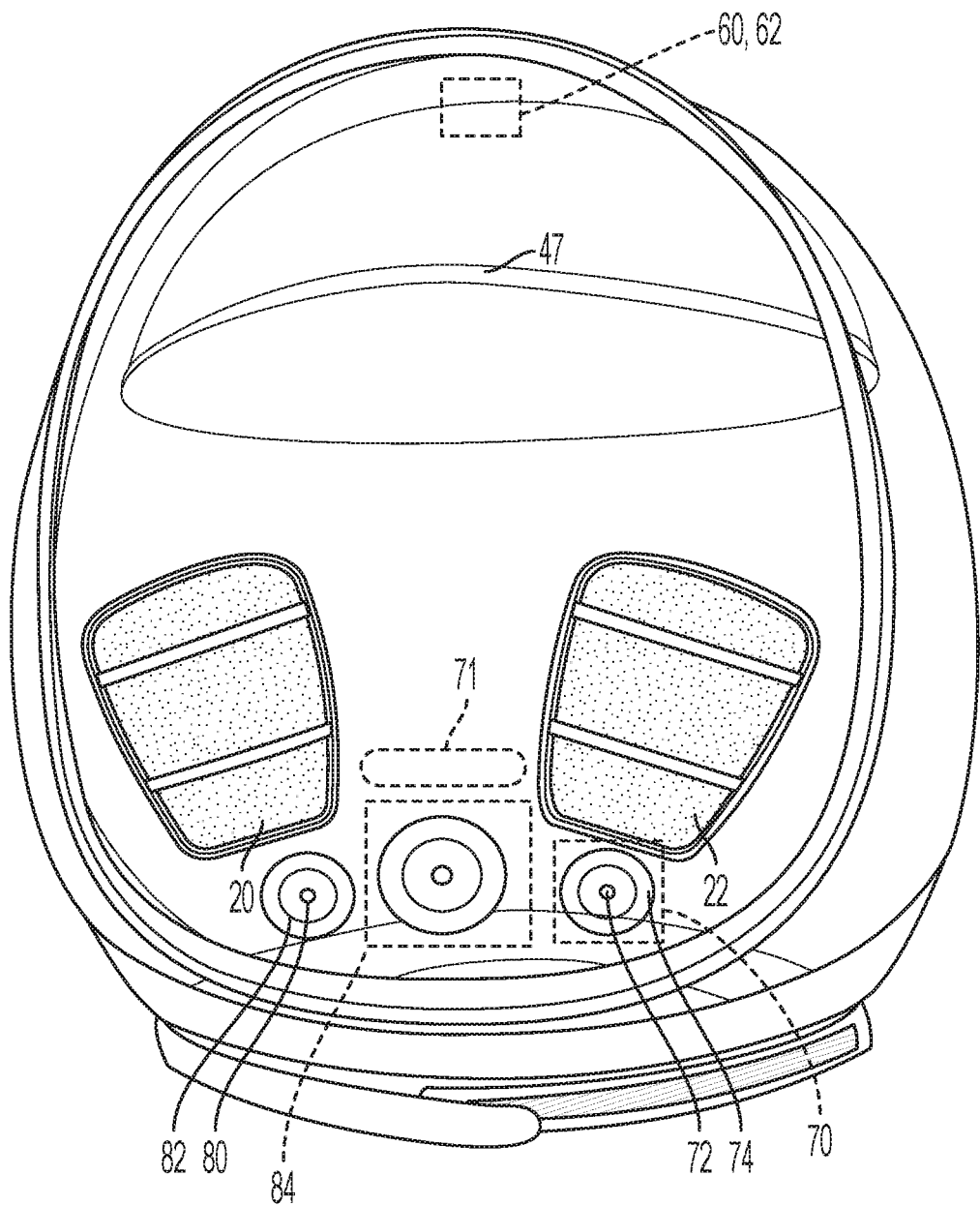
FIG. 5 illustrates a release valve for protecting the user in the event that airflow through the filters is blocked.

The filters 20, 22 may be disposed so that they're offset from the user's mouth. Referring to FIG. 5, the user's mouth 71 may be positioned in the middle of the two filters 20, 22. In this way, when the user's speaks, spit, sneezes, coughs, etc., microorganisms emanating from the user is less likely to contaminate the filters 20, 22. Plus, this area in front of the user's mouth 71 may be transparent to facilitate communication between the user and others.

Figure 2:
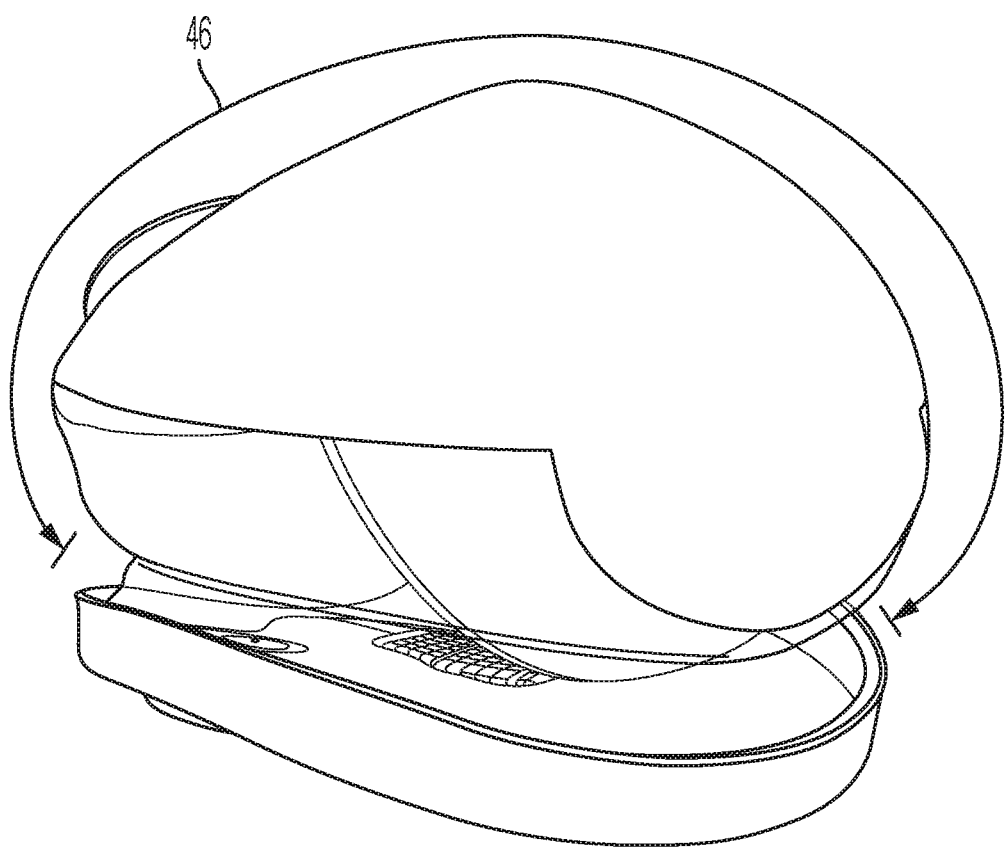
FIG. 2 is a perspective view of the head encapsulation unit shown in FIG. 1 as it is being traversed to an expanded position.
Figure 3:
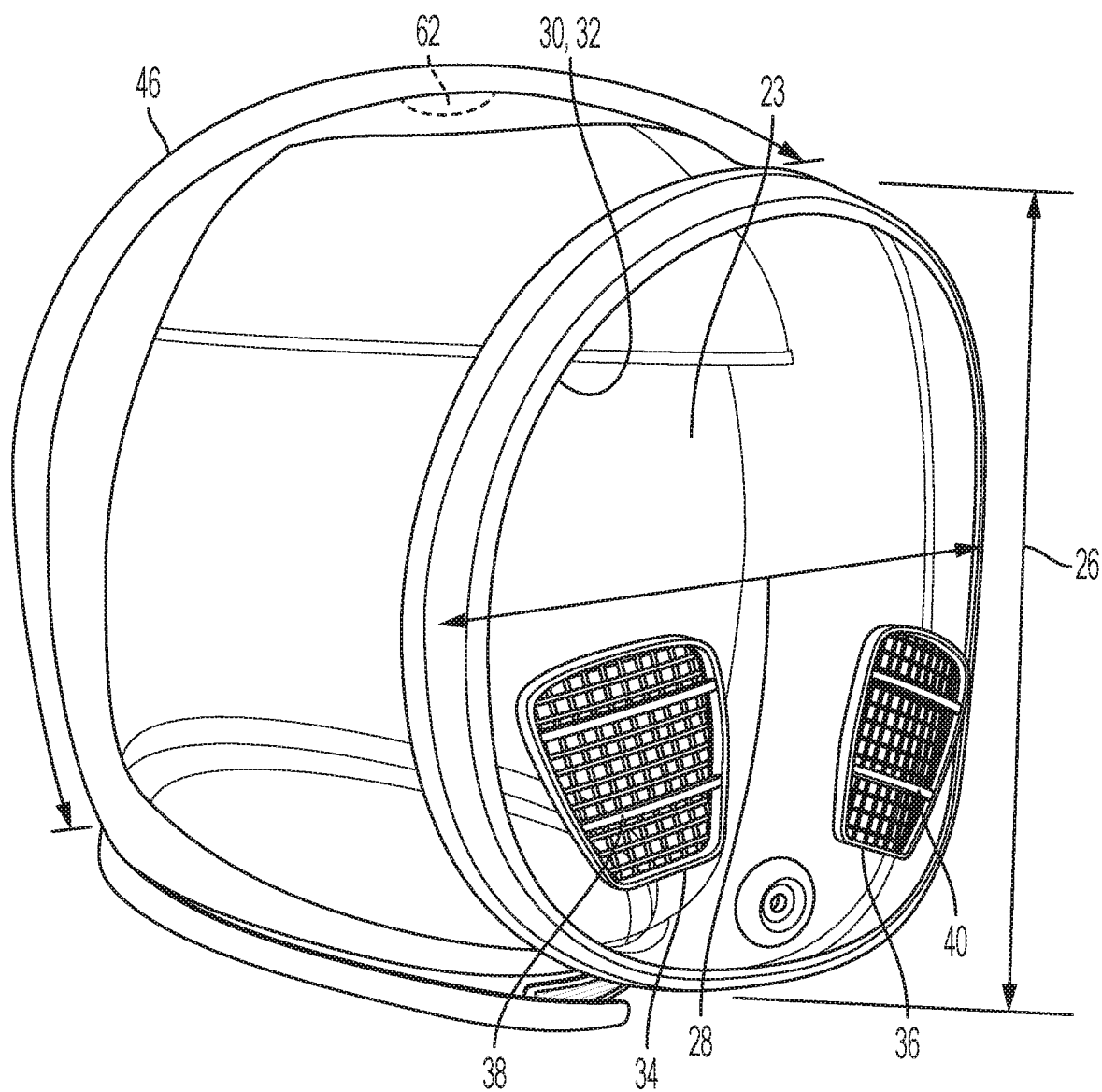
FIG. 3 is a perspective view of the head encapsulation unit shown in FIG. 1 when it is in the expanded position.
Figure 4:
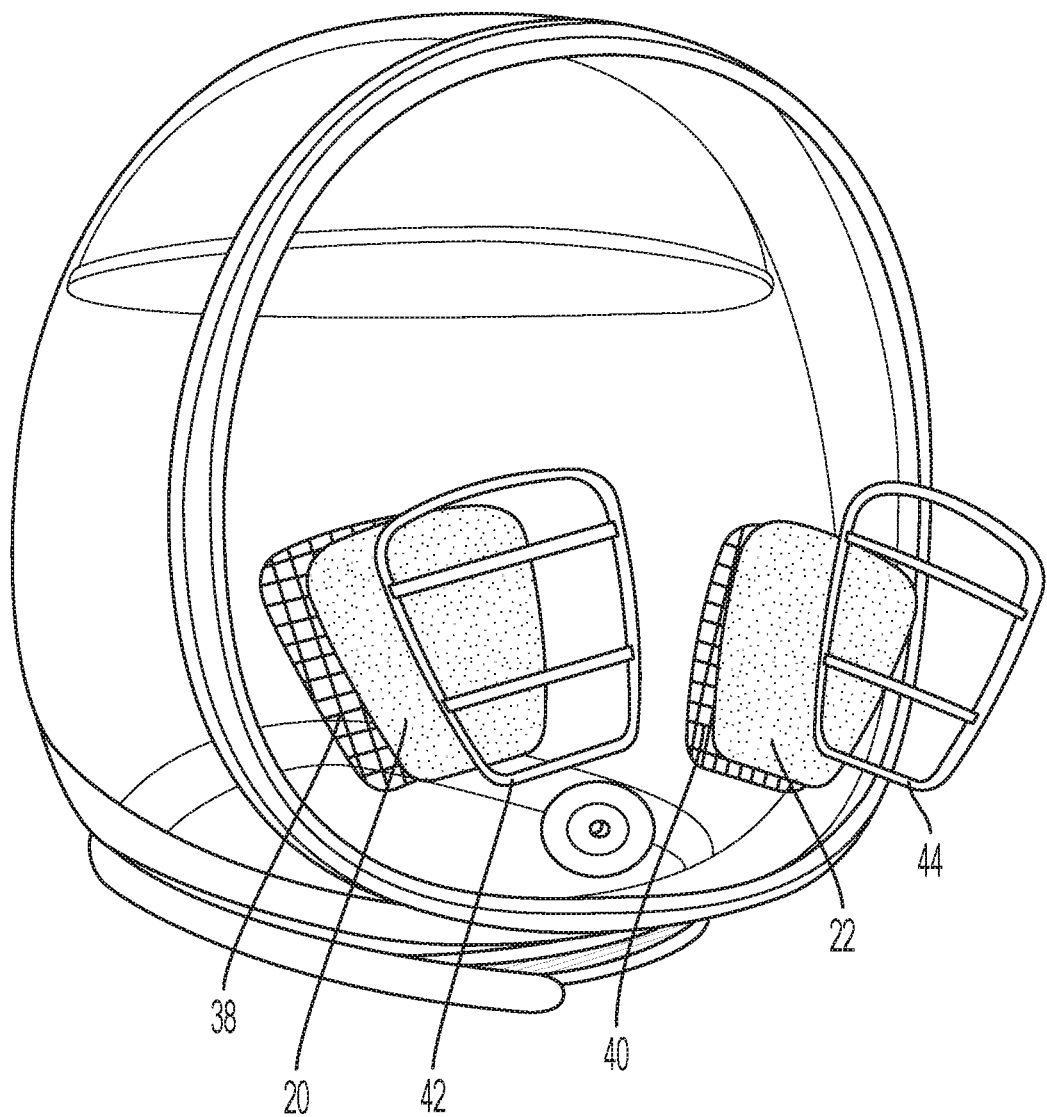
FIG. 4 illustrates filters and mounting brackets for attaching the filters to the head encapsulation unit.

A housing 46 may be attached to the frame 24. The housing 46 may be fabricated from a material that is flexible so that the housing can be traversed to the collapsed position (FIG. 1) from the expanded position (FIG. 7). Moreover, the material from which the housing 46 is fabricated may also be biased in the outward position (FIG. 3). In this regard, in order to traverse the head encapsulation unit 10 from the collapsed position to the expanded position, the user can release an optional strap 50 (FIG. 1). When the strap 50 is released, the housing 46 opens up as shown in the transition illustrated in FIGS. 1-3. As described therein, the housing 48 may be fabricated from a flexible but resilient material that is biased to the expanded position to facilitate the transition of the housing 46 from the collapsed position to the expanded position. However, it is also contemplated that the housing may have thin wire rods that are shaped to the expanded position of the housing 46 and is bendable so that the housing is in the collapsed position. The material from which the housing 46 is fabricated may be a flexible material. The wire rods would be lined or embedded in the housing material so that the housing 46 can be transitioned from the collapsed to the expanded positions without any need to push open the housing with the user's hand. In this regard, when the strap 50 is released or open, the flexible but resilient wire rods do the work of traversing the housing 46 from the collapsed position to the expanded position.

To store the head encapsulation unit 10, the user may press the housing toward the frame 24 then close the strap 50. The strap 50 holds the housing 46 in the collapsed position for transport and/or storage of the head encapsulation unit 10. When the housing 46 is collapsed, the forces from the user's hand works against the outward biasing force of the material and/or the wire rods.

Figure 6:
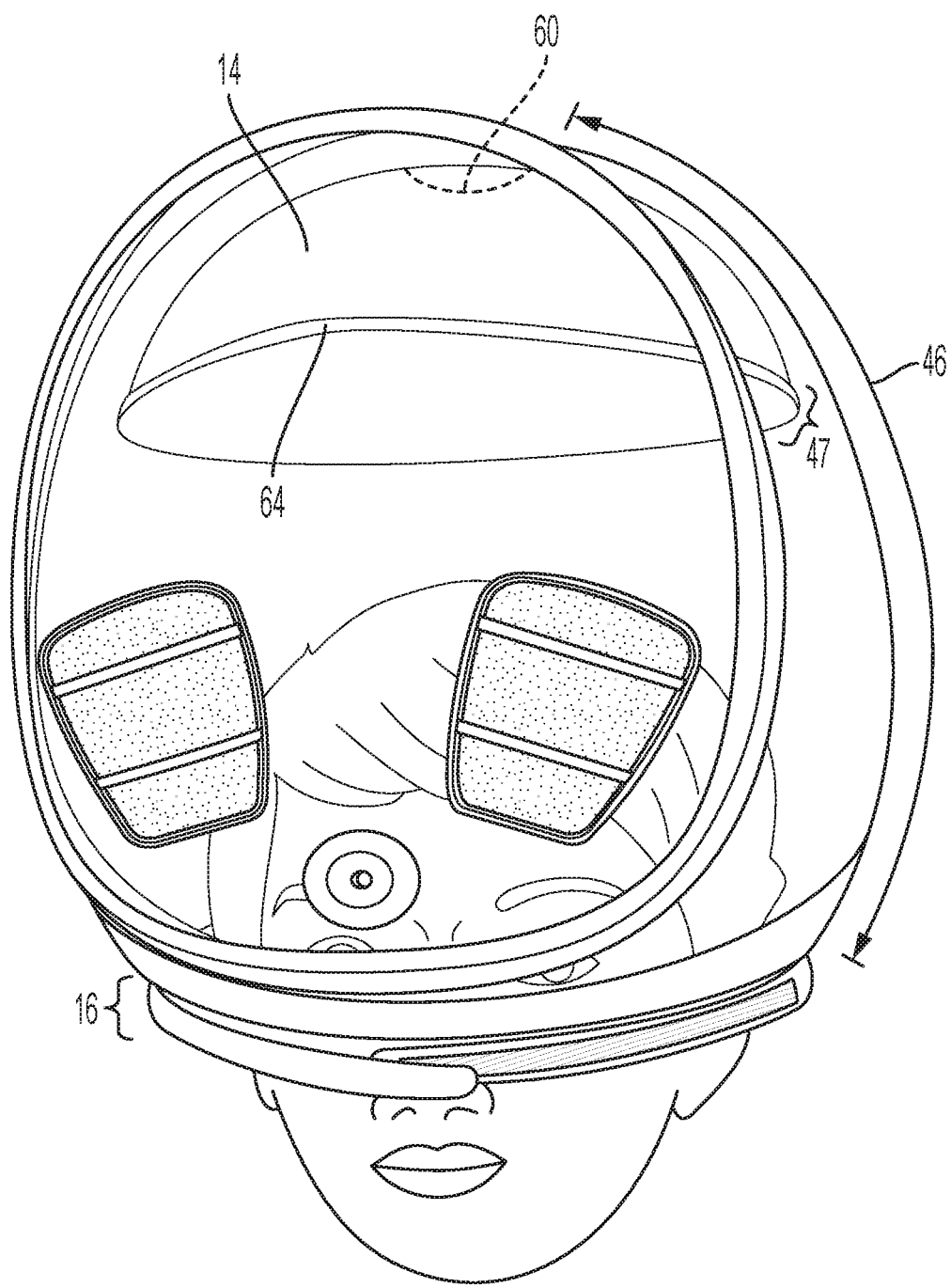
FIG. 6 is a perspective view of the head encapsulation unit in the expanded position with the user inserting his or her head into the head encapsulation unit through a seal.

A bottom portion of the housing 46 may have a seal 16. This seal 16 may be expanded so that the user's head could pass through the seal and be disposed within the interior volume of the head encapsulation unit 10, as shown in FIG. 6. FIG. 6 illustrates the user's head at its widest position (i.e., at the ears) passing through the seal 16. Moreover, the seal 16 can be collapsed to a size of the user's neck 18, as shown in FIG. 7. The seal 16 may be hermetically sealed to the bottom portion of the housing 46. When the seal 16 is collapsed about the circumference of the person's neck, the seal 16 forms a seal with the person's skin to mitigate micro particulates from entering into the interior volume of the head encapsulation unit 10 as a person breathes in and from microorganisms getting out of the unit 10 in case the user is sick and contagious.

Referring now to FIG. 1, the seal may have a strap 54 and the base member 56 on the other end. The strap is removably attachable to the base member 56 by way of hooks and loops and other removably attachable mechanical devices. An inner side of the seal 16 may be lined with a nonporous cushion material 58 such as silicone, vinyl, neoprene or closed cell foam. When the strap 54 is attached to the base 56, the strap 54 places inward pressure so that the cushion 58 applies slight pressure to the person's neck and the cushion forms a seal with the person's neck.

Figure 9:
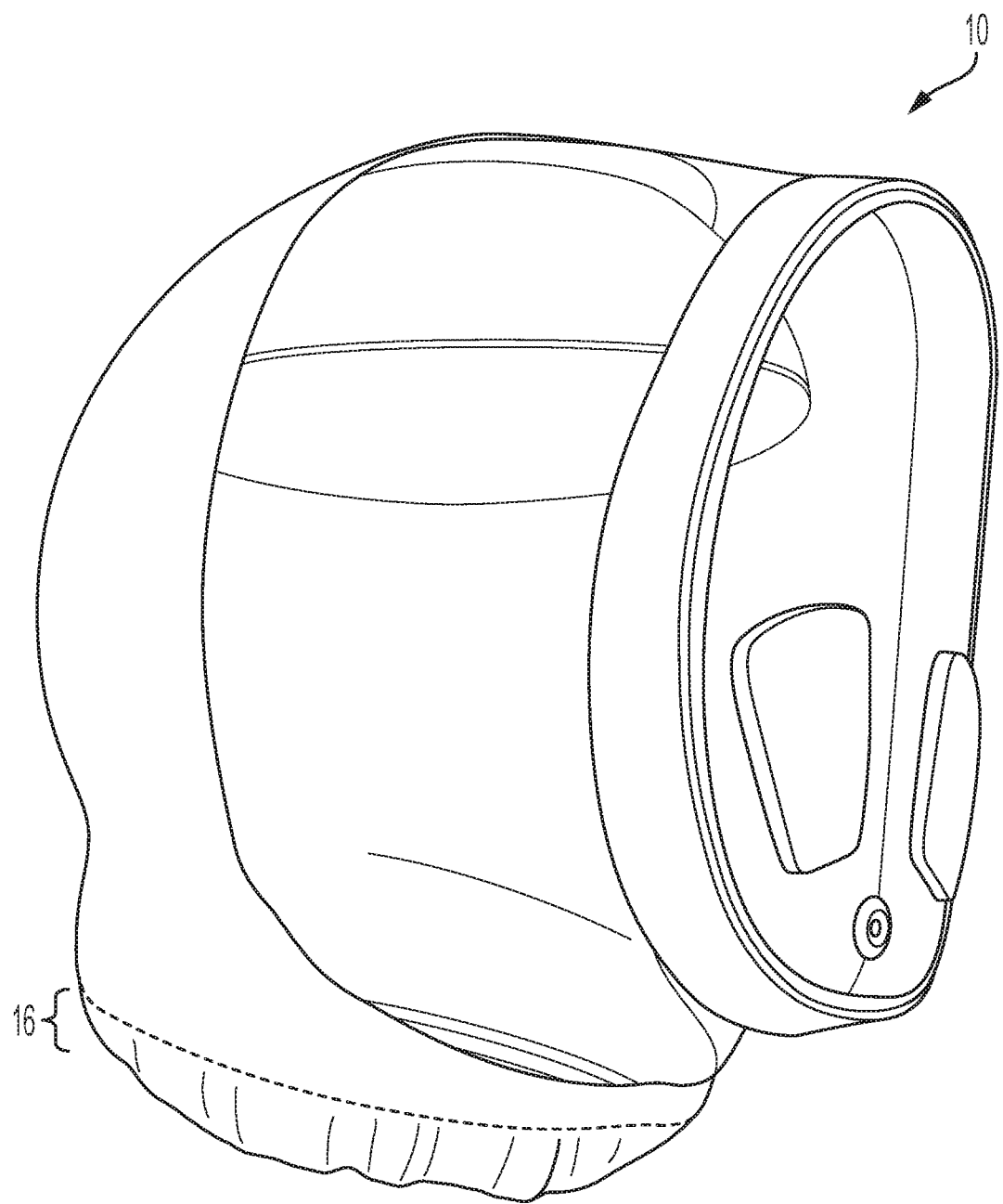
FIG. 9 illustrates an elastic band that expandable and collapsible for allowing the user to put the head encapsulation unit on and seal a bottom portion of the unit to the user's neck.

Alternatively, the seal may be an elastic band as shown in FIG. 9. The elastic band may be sewn into a bottom hem of the housing 46. The bottom portion of the housing when fully expanded can fit a person's head therethrough. Additionally, the elastic band can be stretched out to the fully expanded size of the bottom portion. The elastic band can also contract to the size of the person's neck (e.g., 13, 14, 15, 16 or 17 inches in diameter). The inner side of the seal may have the cushion as discussed herein. The pressure required to pass between the cushion and the person's neck may be greater than the pressure required to pass air through the filters 20, 22.

The housing 46 may have a cap 14. As discussed above, the cap 14 positions the head encapsulation unit on the person's head. The top portion 60 (FIG. 6) of the cap 14 may be secure to the top portion 62 (FIG. 3) of the housing 46 on its interior side, as shown in FIG. 5. The cap may be provided in various sizes to fit a person's head. By way of example and not limitation, the cap 14 may have a band 47 (FIG. 5) which defines a circumference 64 (FIG. 5). The band 47 may be provided in sizes having a circumference between 8 inches and 18 inches. The band 47 of the cap 14 may be elastic so that the circumference 64 may stretch between 8 to 9 inches, 9 to 10 inches, and so forth in 1 inch increments up to 18 inches. The head encapsulation unit 10 may be selected based on the user's head diameter about its forehead so that the cap of the head encapsulation unit fits the user's head.

Referring now to FIG. 6, as the user inserts his or her head through the seal 16 and the bottom portion of the housing, the user may insert his or her head into the cap 14. The cap may be fabricated from a material that is biased to the open position as shown in FIG. 6. When the housing 46 is traversed from the collapsed position to the expanded position, the cap 14 is also traversed from a collapsed position to the open position. When the user wears the cap 14 about his or her head, the seal is positioned at the user's neck. The strap 54 may be wrapped around the user's neck and attached to the base 56 as shown by arrow 66. To close the seal 16, the user may pull on the strap 54 slightly to generate a small force. The strap 54 may then be attached to the base 56. This action provides a slight pressure against the person's neck and the cushion of the strap. The cap 14 and the seal 16 positions the housing 56, the rigid frame 24 and the transparent layer 23 in the proper position so that the head encapsulation unit 10 is comfortable upon the user's head.

The head encapsulation unit 10 may also have a release valve 70. As shown in FIG. 5, the transparent layer 24 may be fitted with the release valve 70. The release valve 70 acts as a protective measure for the user. In the event that the filters 20, 22 are clogged and prevent air from entering or leaving the head encapsulation unit 10, the release valve 70 will burst to allow air to enter and leave the head encapsulation unit 10 to bring air into the head encapsulation unit 10 and to vent carbon dioxide out of the head encapsulation unit 10. The release valve 70 may be fabricated from a frangible material 72. The frangible material may have a burst pressure that is greater than the positive and negative pressures generated within the head encapsulation unit as the person's breaths in and out and the filters 20, 22 are operating within its normal operations. The frangible material may be centrally embedded within a button 74. The button 74 may be embedded into the transparent layer 23.

During use, the head encapsulation unit may be removed from a storage locker. To put the head encapsulation unit on, the user may release a first end of the strap from the frame. Because the housing 46 is biased to the expanded position, the housing begins to transition from the collapsed position (FIG. 1) to the expanded position (FIG. 3). Once the housing 46 is in the expanded position, the user may detach the strap of the seal from the base in the event that it is not already detached. With his or her hands, the user may stretch open the bottom portion of the housing so that the head encapsulation unit can be worn by the user. In particular, the user inserts his or her head into the through-hole formed at the bottom portion of the housing.

Additionally, once the head of the user is inserted into the head encapsulation unit, the user positions a cap of the head encapsulation unit onto the person's head. The cap was unfolded and traversed to the expanded position when the housing 46 was traversed to the expanded position. The cap positions the front transparent layer 24 at the proper distance in front of the user's face. The user can then tension the strap of the seal and attach the strap to the base of the seal. When the strap is attached to the base, a cushion on the interior side of the seal pushes against the skin at the neck of the user. Alternatively, if the unit 10 has the elastic band as shown in FIG. 9, the user may release the bottom portion to allow the elastic band to close the bottom portion, and thus the cushion on the user's neck. The cushion and the neck form a seal to mitigate contaminated air from entering into the inner volume of the head encapsulation unit during use. Also, the head encapsulation unit prevents the user from spreading viruses if and when the user is infected and contagious.

With the head encapsulation unit mounted to the user's head, the user may begin to breathe. When the user breathes in and out, the inner volume has a pressure that increases and decreases. Such pressure under normal circumstances is not sufficient to break the frangible material of the release valve. Plus, the pressure required to pass air through the cushion and the user's neck is greater than the pressure required to pass air through the filters. Additionally, the housing, the frame and the front transparent layer is sufficiently rigid so that the housing doesn't flex in and out but permits air to flow through the filter as the person breathes.

The head encapsulation unit allows the user to talk freely while maintaining a seal at the user's neck. The device does not require specialized fitting to ensure that the seal exists and is maintained during usage. Moreover, when the user speaks or makes facial expressions, since the seal interface is not between the user's face and the mask but the user's neck and the head encapsulation unit, the seal is not broken during normal talking or movements of the person's face.

Referring back to FIG. 5, the transparent layer 24 may have various features to assist the user in communicating with others, to treat the air within the head encapsulation unit and to allow the person to intake fluids. More particular, the area of the transparent layer directly in front of the user's mouth 71 may be fabricated with a thin flexible material. The thin flexible material is between about 1 inch by 1 inch to 4 inches by 4 inches. Since the material is thin and flexible, when the user speaks, the thin flexible material vibrates and allows the sound waves to pass through the thin flexible material. Additionally or alternatively, the transparent layer 24 may be fitted with a microphone 80 and a speaker 82. The microphone 80 may be positioned on an inner side of the transparent layer 24. The speaker 82 may be positioned on an outer side of the transparent layer 24. A battery may be connected to the microphone and speaker to drive the speaker and operate the microphone. Additionally, a speaker 86 may be disposed on the inner side of the transparent layer 24 and may be positioned adjacent to the user's ear. Plus, a receiver 88 (e.g., Bluetooth enabled) may be connected to the speaker. Other people may speak to the user by downloading an app to a smartphone. Other people can start the app then speak into the phone which transmits the voice data to the Bluetooth enabled receiver. The voice data is then communicated to the speaker 86 so that the user can listen to the other person.

A fluid input port 84 may be positioned centrally and immediately below the thin flexible area of the transparent layer 24. The fluid input port allows a user to insert a tube through the transparent layer. The tube may insert oxygen, atomized disinfectant and water. The tube may be operative to carry water so that the user can hydrate him or herself during use without having to remove the head encapsulation unit. The fluid input port may be valve which opens when the tube is pushed against the valve.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A head encapsulation unit for mitigating contact of an airborne virus or bacteria from contacting eyes, nose, ears, mouth, facial hair and head hair and for mitigating spread of virus by a user when the user is infected and contagious, the head encapsulation unit comprising:
    a body fabricated from a resilient and flexible material defining an interior volume, the body including:
        a frame configured to circumscribe a face of the user;
        a bottom portion;
        a housing;
        a transparent front panel having one or more cutouts; and
        a top portion;
    one or more filters attached to the one or more cutouts for allowing air to be expended out of the head encapsulation unit and fresh air to flow into the head encapsulation unit;
    wherein the housing, the frame, and the front transparent panel are sufficiently rigid so that the housing does not flex in and out but permits air to flow through the one or more filters when the user breathes;
    a seal attached to the bottom portion of the body, the seal including:
        a sealing strap;
        a base; and
        cushion;
    wherein the sealing strap is removably attachable to the base, a through hole in the bottom portion of the body being sufficiently large so that a head of the user is insertable through the through hole of the bottom portion to wear the head encapsulation unit, the cushion forming a complete seal against a neck of the user when the sealing strap is pulled and attached to the base to stop contaminated air from entering the interior volume of the body;
    wherein the one or more filters being an only path for flowing gas into and out of the head encapsulation unit when a pressure within the head encapsulation unit is below a threshold pressure.

2. The head encapsulation unit of claim 1 wherein the body is resiliently biased to an expanded position and collapsible to a collapsed position, the head encapsulation unit further comprising a closing strap for holding the housing in the collapsed position, a first end of the closing strap being attached to a first side of the frame of the body, a second end of the closing strap being removably attached to a second side of the frame of the body.

3. The head encapsulation unit of claim 2 wherein at the collapsed position, the head of the user is not disposable in an interior cavity of the housing, and in the expanded position, the head of the user is disposable in the interior cavity of the housing.

4. The head encapsulation unit of claim 3 wherein the transparent front panel comprises a transparent layer attached to the frame, the frame is maintained in a use position when the housing is traversed between the expanded and collapsed positions.

5. The head encapsulation unit of claim 2 wherein the bottom portion is stretchable.

6. The head encapsulation unit of claim 2 further comprising a wire rod frame resiliently biased so that the housing is in the expanded position, the wire rod being bendable to traverse the housing to the collapsed position.

7. The head encapsulation unit of claim 2 wherein the housing of the body is fabricated from a flexible but resilient material.

8. The head encapsulation unit of claim 2 wherein the housing of the body is fabricated from wire rods shaped to the expanded position and is bendable so that the housing is traversable to the collapsed position.

9. The head encapsulation unit of claim 1 wherein the cushion is fabricated from silicone, vinyl, neoprene or a closed cell foam.

10. The head encapsulation unit of claim 1 further comprising a cap which is worn by the user when using the head encapsulation unit for positioning the head encapsulation unit on the head of the user, the cap being attached to the body.

11. The head encapsulation unit of claim 1 further comprising a cap attached to an inside of the body at the top portion for aligning the head encapsulation unit to the user's head.

12. The head encapsulation unit of claim 1 wherein the bottom portion is stretchable to allow the user to insert a head of the user into the interior volume of the body.

13. The head encapsulation unit of claim 1 wherein the cushion is fabricated from silicone, vinyl, neoprene, closed cell foam or combinations thereof.

14. The head encapsulation unit of claim 1 wherein the seal is fabricated from silicone, vinyl, neoprene, closed cell foam or combinations thereof.

* * * * *